United States Patent
Guo et al.

(10) Patent No.: US 12,161,776 B2
(45) Date of Patent: Dec. 10, 2024

(54) ABSORBABLE BONE WAX HAVING FUNCTION OF PROMOTING BONE REPAIR AND PREPARATION METHOD THEREOF

(71) Applicant: GUANGZHOU BEOGENE BIOTECHNOLOGY CO., LTD., Guangdong (CN)

(72) Inventors: Rui Guo, Guangdong (CN); Yong Lan, Guangdong (CN); Yu Liu, Guangdong (CN); Longbao Feng, Guangdong (CN); Yu Chen, Guangdong (CN)

(73) Assignee: GUANGZHOU BEOGENE BIOTECHNOLOGY CO., LTD., Guangzhou (CN)

( * ) Notice: Subject to any disclaimer, the term of this patent is extended or adjusted under 35 U.S.C. 154(b) by 870 days.

(21) Appl. No.: 17/172,103

(22) Filed: Feb. 10, 2021

(65) Prior Publication Data
US 2021/0162093 A1 Jun. 3, 2021

Related U.S. Application Data

(63) Continuation-in-part of application No. PCT/CN2019/102118, filed on Aug. 23, 2019.

(30) Foreign Application Priority Data

Sep. 29, 2018 (CN) .......................... 201811153419.5

(51) Int. Cl.
*A61L 24/04* (2006.01)
*A61L 24/02* (2006.01)
(Continued)

(52) U.S. Cl.
CPC .............. *A61L 24/043* (2013.01); *A61L 24/02* (2013.01); *A61L 2430/02* (2013.01); *C08L 1/04* (2013.01);
(Continued)

(58) Field of Classification Search
CPC .... A61L 24/043; A61L 24/02; A61L 2430/02; A61L 24/0084; A61L 24/08;
(Continued)

(56) References Cited

U.S. PATENT DOCUMENTS 9,512,277 B2 * 12/2016 Gorna .................. A61L 24/046

FOREIGN PATENT DOCUMENTS

| CN | 103071447 A | 5/2013 |
| CN | 105521525 A | 4/2016 |

(Continued)

OTHER PUBLICATIONS

The Coprecipitation of Strontium with Hydroxyapatite FujinoOsamu Bulletin of the Chemical Society of Japan 1975 48:5, 1455-1458 (Year: 1975).*

(Continued)

*Primary Examiner* — Walter E Webb
*Assistant Examiner* — Amanda Michelle Petritsch

(57) ABSTRACT

The invention discloses absorbable bone wax having a function of promoting bone repair and a preparation method thereof, falling within the technical field of biomedical materials. The absorbable bone wax comprises the following components in mass percentage: 10%~50% polyoxypropylene polyoxyethylene block copolymer, 50%~90% polyoxypropylene polyoxyethylene random copolymer, 0%~20% strontium substituted hydroxyapatite and 0%~20% microcrystalline cellulose. The absorbable bone wax has good biocompatibility and degradability, can provide good physiological conditions for absorption in vivo, has excellent mechanical and hemostatic properties, and promotes bone repair.

5 Claims, 4 Drawing Sheets

(51) Int. Cl.
*C08L 1/04* (2006.01)
*C08L 71/02* (2006.01)

(52) U.S. Cl.
CPC ............ *C08L 71/02* (2013.01); *C08L 2203/02* (2013.01); *C08L 2205/025* (2013.01)

(58) Field of Classification Search
CPC ............. A61L 24/0042; A61L 2400/04; A61L 24/0015; A61L 24/046; A61L 2300/112; A61L 2300/412; C08L 1/04; C08L 71/02; C08L 2203/02; C08L 2205/025
See application file for complete search history.

(56) References Cited

FOREIGN PATENT DOCUMENTS

| CN | 105816905 A | * | 8/2016 | ......... A61L 24/0015 |
| CN | 107308487 A | * | 11/2017 | |
| CN | 107519528 A | | 12/2017 | |

OTHER PUBLICATIONS

Osamu Fujino, The Coprecipitation of Strontium with Hydroxyapatite, Bulletin of the Chemical Society of Japan, 48:5, 1455-1458 (Year: 1975).*
Test methods for primary wound dressing—Part 4: Conformability, Pharmaceutical Industry Standard of the People's Republic of China, Mar. 23, 2004, pp. 1-2, YY/T 0471.4-2004.
International Search Report of PCT Patent Application No. PCT/CN2019/102118 issued on Oct. 24, 2019.

* cited by examiner

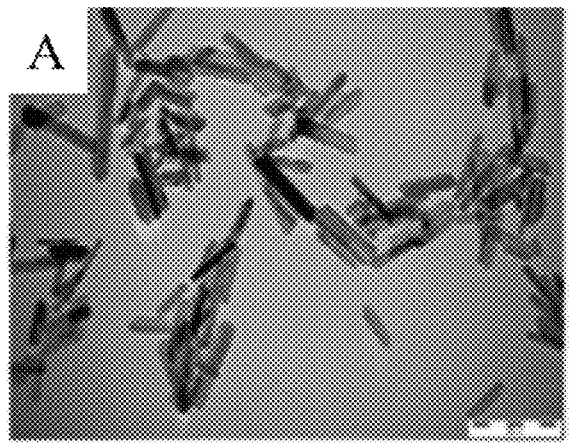 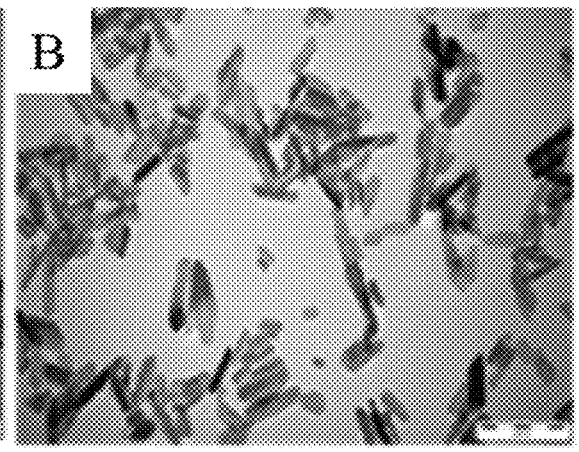
FIG. 1A  FIG. 1B
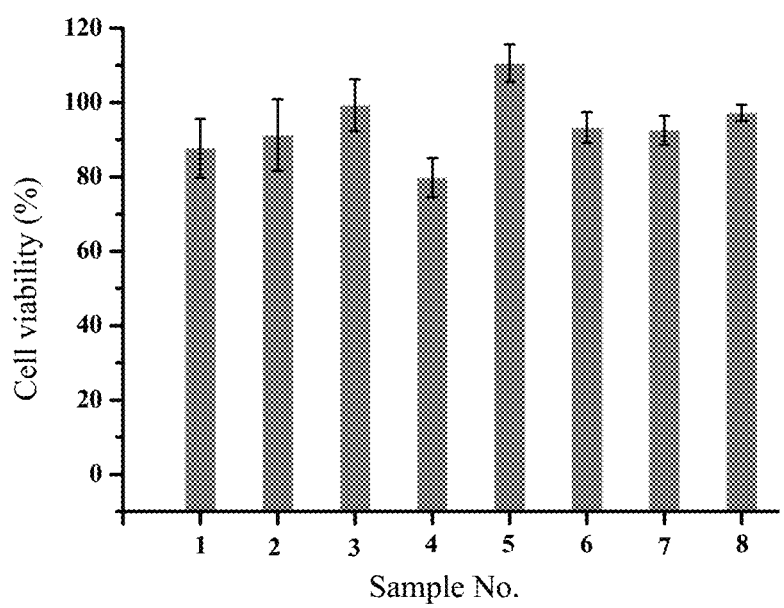
FIG. 2

ABSORBABLE BONE WAX HAVING FUNCTION OF PROMOTING BONE REPAIR AND PREPARATION METHOD THEREOF

CROSS REFERENCE TO RELATED APPLICATIONS

The present application is a Continuation-in-Part Application of PCT Application No. PCT/CN2019/102118 filed on Aug. 23, 2019, which claims the benefit of Chinese Patent Application No. 201811153419.5 filed on Sep. 29, 2018. All the above are hereby incorporated by reference in their entirety.

FIELD OF THE INVENTION

The present invention relates to the technical field of biomedical materials, and in particular to absorbable bone wax having a function of promoting bone repair and a preparation method thereof.

BACKGROUND OF THE INVENTION

Bone hemorrhage occurs during many traumas and surgical procedures. Therefore, it is necessary to control bone hemorrhage or perform bone hemostasis. Bone wax is a kind of bone hemostatic material, and is used to control local bone hemorrhage by applying the bone wax on cutting surfaces during surgery. At present, the bone wax widely used in surgical operations is mostly prepared from beeswax by mixing beeswax with water-insoluble hydrocarbons and vegetable oils. The disadvantage of such bone wax is poor adhesion and high brittleness at room temperature. However, the widely used bone wax is non-absorbable by the human body. When used in surgery, such bone wax will stay at the application site for a long time, which will cause not only chronic inflammation but also foreign body reactions, cause non-healing interstitial bacterial infection and increase a risk of bone infection, and inhibit the bone healing process due to the non-renewable nature of such bone wax. In addition, traditional bone wax cannot effectively repair defective bone parts in the process of bone hemostasis. Therefore, it is not suitable for parts that require bone regeneration and/or fusion, and it cannot be used in contaminated parts. In order to overcome these shortcomings of traditional bone wax, a research on absorbable bone wax having a function of promoting bone repair is imminent.

SUMMARY OF THE INVENTION

The purposes of the present invention are provide absorbable bone wax having a function of promoting bone repair and a preparation method thereof to overcome the shortcomings of the prior art. Main components of existing bone wax are improved in the absorbable bone wax, so that the absorbable bone wax has improved bioavailability and mechanical property and enhanced degradability, reduces the possibility of local infection due to bone wax, and promotes repair of bone defects.

To achieve the above purposes, the technical solution adopted by the present invention includes the following aspects.

In one aspect, absorbable bone wax having a function of promoting bone repair comprises the following components in mass percentage: 10%~50% polyoxypropylene polyoxyethylene block copolymer, 50%~90% polyoxypropylene polyoxyethylene random copolymer, 0%~20% strontium substituted hydroxyapatite and 0%~20% microcrystalline cellulose.

In the present invention, the polyoxypropylene polyoxyethylene block copolymer and the polyoxypropylene polyoxyethylene random copolymer are used as main raw materials of the absorbable bone wax. The polyoxypropylene polyoxyethylene block copolymer and the polyoxypropylene polyoxyethylene random copolymer are absorbable polymer materials with a good hemostatic effect because of advantages of non-toxic, non-irritating, good biocompatibility, controllable degradation through processing and modification, easily-absorbable degradation products and low immunoantigenicity.

Microcrystalline cellulose is a crystal obtained by acid hydrolysis of cellulose. It has properties of high strength, low thermal expansion coefficient, renewability, and good biocompatibility and degradability, as well as high crystallinity and non-toxicity.

Hydroxyapatite is the main inorganic component of human bones and animal bones. It can achieve chemical bond bonding with body tissues at interfaces. It has a certain solubility in living organism, and can release ions that are harmless to the living organism, participate in metabolism of the living organism, stimulate or induce bone regeneration, promote repair of defective tissues, and show biological activity. However, it also has shortcomings such as brittleness, poor degradability, and low osteoinductivity. Strontium substituted hydroxyapatite can further improve the properties of hydroxyapatite itself. It not only has good mechanical properties and biological properties, but also can promote osteoblast activity and inhibit osteoclast differentiation and can also promote formation of new bones.

In the present invention, the polyoxypropylene polyoxyethylene block copolymer, the polyoxypropylene polyoxyethylene random copolymer, the strontium substituted hydroxyapatite and the microcrystalline cellulose are compounded; and the polyoxypropylene polyoxyethylene block copolymer and the polyoxypropylene polyoxyethylene random copolymer which possess good biocompatibility function as raw materials of the absorbable bone wax, which enhances degradability in living organism, facilitating absorption; addition of the strontium substituted hydroxyapatite can promote the absorbable bone wax to repair bone defects; and nano-microcrystalline cellulose is used to improve solubility and mechanical properties of insoluble drugs in water. The absorbable bone wax of the present invention has good biocompatibility and degradability, provides good physiological conditions for absorption in vivo, has good mechanical properties and hemostatic properties, and also promotes bone repair.

As a preferred embodiment of the absorbable bone wax having a function of promoting bone repair according to the present invention, the absorbable bone wax comprises the following components in mass percentage: 10%~30% polyoxypropylene polyoxyethylene block copolymer, 50%~65% polyoxypropylene polyoxyethylene random copolymer, 2.5%~20% strontium substituted hydroxyapatite and 2%~20% microcrystalline cellulose.

As a preferred embodiment of the absorbable bone wax having a function of promoting bone repair according to the present invention, the absorbable bone wax comprises the following components in mass percentage: 30% polyoxypropylene polyoxyethylene block copolymer, 65% polyoxypropylene polyoxyethylene random copolymer, 2% strontium substituted hydroxyapatite and 3% microcrystalline cellulose.

As a preferred embodiment of the absorbable bone wax having a function of promoting bone repair according to the present invention, the absorbable bone wax comprises the following components in mass percentage: 30% polyoxypropylene polyoxyethylene block copolymer, 65% polyoxypropylene polyoxyethylene random copolymer, 2.5% strontium substituted hydroxyapatite and 2.5% microcrystalline cellulose.

In the present invention, the amounts of the polyoxypropylene polyoxyethylene block copolymer, the polyoxypropylene polyoxyethylene random copolymer, the strontium substituted hydroxyapatite and the microcrystalline cellulose are optimized to further improve bioavailability and degradability, reduce the possibility of local infections due to bone wax, improve mechanical properties, and promote repair of bone defects.

As a preferred embodiment of the absorbable bone wax having a function of promoting bone repair according to the present invention, a molecular weight of the polyoxypropylene polyoxyethylene block copolymer is in a range from 4,400 to 14,600; and a molecular weight of the polyoxypropylene polyoxyethylene random copolymer is in a range from 2,500 to 12,000.

As a preferred embodiment of the absorbable bone wax having a function of promoting bone repair according to the present invention, a molar ratio of Sr/(Sr+Ca) in the strontium substituted hydroxyapatite is in a range from 10% to 50%.

As a preferred embodiment of the absorbable bone wax having a function of promoting bone repair according to the present invention, the strontium substituted hydroxyapatite is strontium substituted nano-hydroxyapatite, and the strontium substituted nano-hydroxyapatite is prepared by a co-precipitation method.

As a preferred embodiment of the absorbable bone wax having a function of promoting bone repair according to the present invention, the microcrystalline cellulose is nano-crystalline cellulose.

The nano-crystalline cellulose has properties of small particle size, high strength, low thermal expansion coefficient, renewability, and good biocompatibility and degradability, as well as high crystallinity, non-toxicity, and large specific surface area, thus it is beneficial to improvement of mechanical properties of the absorbable bone wax.

In another aspect, the present invention also provides a preparation method of the above-mentioned absorbable bone wax having a function of promoting bone repair, comprising the following steps:

(1) Mixing polyoxypropylene polyoxyethylene block copolymer and polyoxypropylene polyoxyethylene random copolymer, and heating to a temperature in a range from 60° C. to 100° C. under a condition of mechanical stirring so that a resultant mixture is in a liquid state and is mixed well;

(2) While maintaining the condition of mechanical stirring and heating, adding microcrystalline cellulose, β-cyclodextrin and strontium substituted hydroxyapatite into a well-mixed liquid mixture in step (1), and stirring and mixing well;

(3) Putting a well-mixed mixture in step (2) in a mold or sub-packaged bottle, and leaving the mold or sub-packaged bottle at room temperature for 2 hours for curing and forming; and (4) Packaging and sealing a cured and formed product, and sterilizing it by autoclaving or γ-ray to obtain the absorbable bone wax.

Compared with the prior art, the beneficial effects of the present invention are shown as follows:

The absorbable bone wax of the present invention has good biocompatibility and good degradability, provides good physiological conditions for absorption in vivo, has good mechanical properties and hemostatic properties, and also promotes bone repair. The preparation method of the present invention is simple to operate, and the raw materials required are easily available, and the absorbable bone wax prepared are expected to be widely used in the field of biomedical engineering materials.

BRIEF DESCRIPTION OF THE DRAWINGS

FIGS. 1A and 1B are transmission electron micrographs of nano-hydroxyapatite (A) prepared in Comparative Example 1 and strontium substituted nano-hydroxyapatite (B) prepared in Example 1;

FIG. 2 is a graph of cell activity of bone wax of Example 1 to Example 5;

Figure 3:
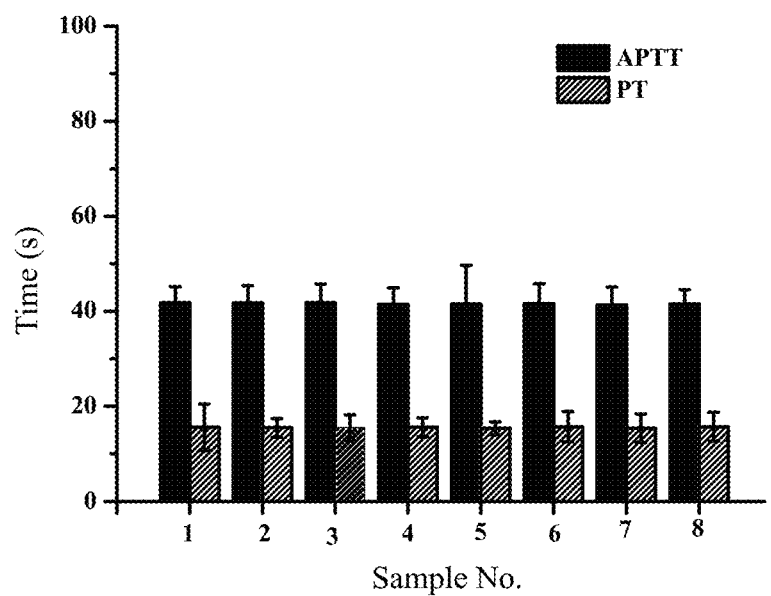
FIG. 3 is APTT and PT diagrams of bone wax of Example 1 to Example 5.
Figure 4A:
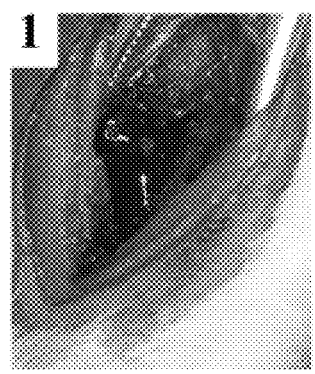
FIGS. 4A-4E are diagrams respectively showing hemostatic effects in vivo of bone wax of Example 1 to Example 5.
Figure 4B:
Figure 4C:
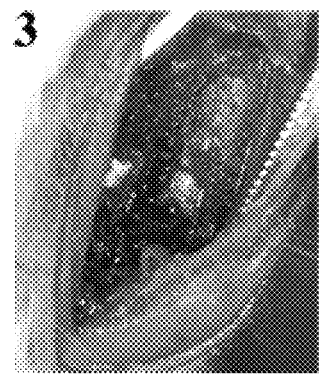
Figure 4D:
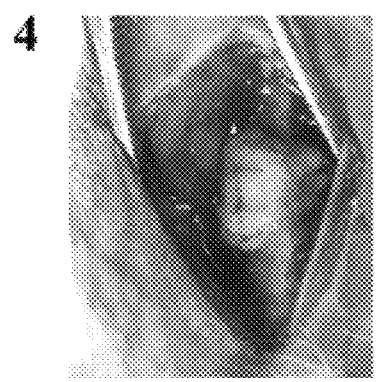
Figure 4E:
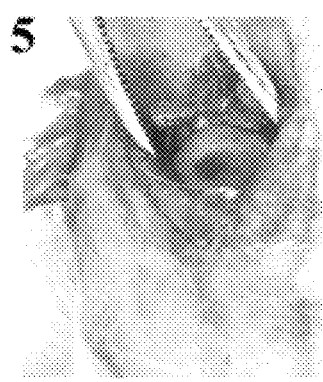

In the figures, 1 represents absorbable bone wax of Example 1; 2 represents absorbable bone wax of Example 2; 3 represents absorbable bone wax of Example 3; 4 represents absorbable bone wax of Example 4; 5 represents absorbable bone wax of Example 5; 6 represents absorbable bone wax of Example 6; 7 represents absorbable bone wax of Example 7; and 8 represents absorbable bone wax of Example 8.

DETAILED DESCRIPTION OF THE INVENTION

In order to better illustrate the purposes, the technical solutions and the advantages of the present invention, the present invention will be further described below in conjunction with specific embodiments. Those skilled in the art should understand that the specific embodiments described herein are only used to explain the present invention, but not to limit the present invention.

In the examples, the experimental methods used are conventional methods, unless otherwise specified, and the materials and reagents used, unless otherwise specified, can be obtained from commercial sources.

EXAMPLE 1

As an example of the absorbable bone wax having a function of promoting bone repair according to the present invention, the absorbable bone wax having a function of promoting bone repair described in this example comprises polyoxypropylene polyoxyethylene block copolymer and polyoxypropylene polyoxyethylene random copolymer in a weight ratio of 30:65, wherein the molecular weight of the polyoxypropylene polyoxyethylene block copolymer is 4,400; and the molecular weight of the polyoxypropylene polyoxyethylene random copolymer is 12,000.

The preparation method of the absorbable bone wax having a function of promoting bone repair in this example includes the following steps:
(1) Mixing the polyoxypropylene polyoxyethylene block copolymer and the polyoxypropylene polyoxyethylene random copolymer, and heating to 80° C. under a condition of mechanical stirring so that a resultant mixture is in a liquid state and is mixed well;
(2) Putting the well-mixed mixture in a mold or sub-packaged bottle, and leaving the mold or sub-packaged bottle at room temperature for 2 hours for curing and forming; and
(3) Packaging and sealing the cured and formed product and sterilizing it by autoclaving or γ-ray to obtain the absorbable bone wax.

EXAMPLE 2

As an example of the absorbable bone wax having a function of promoting bone repair according to the present invention, the absorbable bone wax having a function of promoting bone repair described in this example comprises the following components in mass percentage: 30% polyoxypropylene polyoxyethylene block copolymer, 65% polyoxypropylene polyoxyethylene random copolymer and 5% nano-crystalline cellulose, wherein the molecular weight of the polyoxypropylene polyoxyethylene block copolymer is 4,400; and the molecular weight of the polyoxypropylene polyoxyethylene random copolymer is 12,000.

The preparation method of the absorbable bone wax having a function of promoting bone repair in this example includes the following steps:
(1) Mixing the polyoxypropylene polyoxyethylene block copolymer and the polyoxypropylene polyoxyethylene random copolymer, and heating to 80° C. under a condition of mechanical stirring so that a resultant mixture is in a liquid state and is mixed well;
(2) Under the condition of mechanical stirring and heating, adding nano-microcrystalline cellulose to the well-mixed liquid mixture in step (1), and stirring and mixing well;
(3) Putting the well-mixed mixture in step (2) in a mold or sub-packaged bottle, and leaving the mold or sub-packaged bottle at room temperature for 2 hours for curing and forming; and
(4) Packaging and sealing the cured and formed product and sterilizing it by autoclaving or γ-ray to obtain the absorbable bone wax.

EXAMPLE 3

As an example of the absorbable bone wax having a function of promoting bone repair according to the present invention, the absorbable bone wax having a function of promoting bone repair described in this example comprises the following components in mass percentage: 30% polyoxypropylene polyoxyethylene block copolymer, 65% polyoxypropylene polyoxyethylene random copolymerand, 5% strontium substituted nano-hydroxyapatite, wherein the molar ratio of Sr/(Sr+Ca) in the strontium substituted nano-hydroxyapatite is 10%; the molecular weight of the polyoxypropylene polyoxyethylene block copolymer is 4,400; and the molecular weight of the polyoxypropylene polyoxyethylene random copolymer is 12,000.

The preparation method of the strontium substituted nano-hydroxyapatite described in this example includes the following steps:
1) Weighing a certain amount of $Ca(NO_3)_2 \cdot 4H_2O$ and dissolving it with deionized water in a beaker, weighing a certain amount of $Sr(NO_3)_2$ and dissolving it with deionized water in another beaker, adding $Sr(NO_3)_2$ solution into $Ca(NO_3)_2 \cdot 4H_2O$ suspension, adjusting the pH value of the resultant suspension of $Ca(NO_3)_2 \cdot 4H_2O$ and $Sr(NO_3)_2$ to be 11 or greater using $NH_3 \cdot H_2O$ solution, and then adding an appropriate amount of SDS to the resultant suspension, and mechanically stirring the solution containing $Ca^{2+}$ and $Sr^{2+}$;
2) Weighing a certain amount of $(NH_4)_2HPO_4$ and dissolving it in a beaker with deionized water to form a solution containing P;
3) Adding the $(NH_4)_2HPO_4$ solution dropwise into the solution containing $Ca^{2+}$ and $Sr^{2+}$ within 40 minutes, wherein the molar ratio of (Ca+Sr) to P in the final solution is 1.67; and transferring the resultant mixture into a high-pressure reactor for incubation for 8 hours at 180° C., then cooling to about 25° C.;
4) Centrifuging the resultant solution at 10,000 rpm for 10 minutes, then performing pumping filtration, and washing sediment with deionized water and ethanol repeatedly; and
5) Drying the sediment in an oven at 80° C. for 12 hours and grinding it to obtain strontium substituted nano-hydroxyapatite (Sr-nHAp).

The preparation method of the absorbable bone wax having a function of promoting bone repair in this example includes the following steps:
(1) Mixing the polyoxypropylene polyoxyethylene block copolymer and the polyoxypropylene polyoxyethylene random copolymer, and heating to 80° C. under a condition of mechanical stirring so that a resultant mixture is in a liquid state and is mixed well;
(2) Under the condition of mechanical stirring and heating, adding strontium substituted nano-hydroxyapatite to the well-mixed liquid mixture in step (1), and stirring and mixing well;
(3) Putting the well-mixed mixture in a mold or sub-packaged bottle, and leaving the mold or sub-packaged bottle at room temperature for 2 hours for curing and forming; and
(4) Packaging and sealing the cured and formed product and sterilizing it by autoclaving or γ-ray to obtain the absorbable bone wax.

EXAMPLE 4

As an example of the absorbable bone wax having a function of promoting bone repair according to the present invention, the absorbable bone wax having a function of promoting bone repair described in this example comprises the following components in mass percentage: 30% polyoxypropylene polyoxyethylene block copolymer, 65% polyoxypropylene polyoxyethylene random copolymer, 3% strontium substituted nano-hydroxyapatite and 2% nano-microcrystalline cellulose, wherein the molar ratio of Sr/(Sr+Ca) in the strontium substituted nano-hydroxyapatite is 10%; the molecular weight of the polyoxypropylene polyoxyethylene block copolymer is 4,400; and the molecular weight of the polyoxypropylene polyoxyethylene random copolymer is 12,000.

The preparation method of the strontium substituted nano-hydroxyapatite described in this example includes the following steps:
1) Weighing a certain amount of $Ca(NO_3)_2 \cdot 4H_2O$ and dissolving it with deionized water in a beaker, weighing a certain amount of $Sr(NO_3)_2$ and dissolving it with deionized water in another beaker, adding $Sr(NO_3)_2$ solution into $Ca(NO_3)_2 \cdot 4H_2O$ suspension, adjusting the pH value of the resultant suspension of $Ca(NO_3)_2 \cdot 4H_2O$ and $Sr(NO_3)_2$ to be 11 or greater using $NH_3 \cdot H_2O$ solution, and then adding an appropriate amount of SDS to the resultant suspension, and mechanically stirring the solution containing $Ca^{2+}$ and $Sr^{2+}$;
2) Weighing a certain amount of $(NH_4)_2HPO_4$ and dissolving it in a beaker with deionized water to form a solution containing P;
3) Adding the $(NH_4)_2HPO_4$ solution dropwise into the solution containing $Ca^{2+}$ and $Sr^{2+}$ within 40 minutes, wherein the molar ratio of (Ca+Sr) to P in the final solution is 1.67; and transferring the resultant mixture into a high-pressure reactor for incubating for 8 hours at 180° C., then cooling to about 25° C.;
4) Centrifuging the resultant solution at 10,000 rpm for 10 minutes, then performing pumping filtration, and washing sediment with deionized water and ethanol repeatedly; and
5) Drying the sediment in an oven at 80° C. for 12 hours and grinding it to obtain strontium substituted nano-hydroxyapatite (Sr-nHAp).

The preparation method of the absorbable bone wax with function of promoting bone repair in this example includes the following steps:
(1) Mixing the polyoxypropylene polyoxyethylene block copolymer and the polyoxypropylene polyoxyethylene random copolymer, and heating to 80° C. under a condition of mechanical stirring so that a resultant mixture is in a liquid state and is mixed well;
(2) Under the condition of mechanical stirring and heating, adding nano-microcrystalline cellulose and strontium substituted nano-hydroxyapatite to the well-mixed liquid mixture in step (1), and then stirring and mixing well;
(3) Putting the well-mixed mixture in a mold or sub-packaged bottle, and leaving the mold or sub-packaged bottle at room temperature for 2 hours for curing and forming; and
(4) Packaging and sealing the cured and formed product and sterilizing it by autoclaving or γ-ray to obtain the absorbable bone wax.

EXAMPLE 5

As an example of the absorbable bone wax having a function of promoting bone repair according to the present invention, the absorbable bone wax having a function of promoting bone repair described in this example comprises the following components in mass percentage: 30% polyoxypropylene polyoxyethylene block copolymer, 65% polyoxypropylene polyoxyethylene random copolymer, 2.5% strontium substituted nano-hydroxyapatite and 2.5% nano-microcrystalline cellulose, wherein the molar ratio of Sr/(Sr+Ca) in the strontium substituted nano-hydroxyapatite is 10%; the molecular weight of the polyoxypropylene polyoxyethylene block copolymer is 4,400; and the molecular weight of the polyoxypropylene polyoxyethylene random copolymer is 12,000.

The preparation method of the strontium substituted nano-hydroxyapatite described in this example includes the following steps:
1) Weighing a certain amount of $Ca(NO_3)_2 \cdot 4H_2O$ and dissolving it with deionized water in a beaker, weighing a certain amount of $Sr(NO_3)_2$ and dissolving it with deionized water in another beaker, adding $Sr(NO_3)_2$ solution into $Ca(NO_3)_2 \cdot 4H_2O$ suspension, adjusting the pH value of the resultant suspension of $Ca(NO_3)_2 \cdot 4H_2O$ and $Sr(NO_3)_2$ to be 11 or greater using $NH_3 \cdot H_2O$ solution, and then adding an appropriate amount of SDS to the resultant suspension, and mechanically stirring the solution containing $Ca^{2+}$ and $Sr^{2+}$;
2) Weighing a certain amount of $(NH_4)_2HPO_4$ and dissolving it in a beaker with deionized water to form a solution containing P;
3) Adding the $(NH_4)_2HPO_4$ solution dropwise into the solution containing $Ca^{2+}$ and $Sr^{2+}$ within 40 minutes, wherein the molar ratio of (Ca+Sr) to P in the final solution is 1.67; and transferring the resultant mixture into a high-pressure reactor for incubating for 8 hours at 180° C., then cooling it to about 25° C.;
4) Centrifuging the resultant solution at 10,000 rpm for 10 minutes, then performing pumping filtration, and washing sediment with deionized water and ethanol repeatedly; and
5) Drying the sediment in an oven at 80° C. for 12 hours and grinding it to obtain strontium substituted nano-hydroxyapatite (Sr-nHAp).

The preparation method of the absorbable bone wax having a function of promoting bone repair in this example includes the following steps:
(1) Mixing the polyoxypropylene polyoxyethylene block copolymer and the polyoxypropylene polyoxyethylene random copolymer, and heating to 80° C. under a condition of mechanical stirring so that a resultant mixture is in a liquid state and is mixed well;
(2) Under the condition of mechanical stirring and heating, adding nano-microcrystalline cellulose and strontium substituted nano-hydroxyapatite to the well-mixed liquid mixture in step (1), and then stirring and mixing well;
(3) Putting the well-mixed mixture in a mold or sub-packaged bottle, and leaving the mold or sub-packaged bottle at room temperature for 2 hours for curing and forming; and
(4) Packaging and sealing the cured and formed product and sterilizing it by autoclaving or γ-ray to obtain the absorbable bone wax.

EXAMPLE 6

As an example of the absorbable bone wax having a function of promoting bone repair according to the present invention, the absorbable bone wax having a function of promoting bone repair described in this example comprises the following components in mass percentage: 10% polyoxypropylene polyoxyethylene block copolymer, 90% polyoxypropylene polyoxyethylene random copolymer, 0% strontium substituted hydroxyapatite, and 0% microcrystalline cellulose, wherein the molecular weight of the polyoxypropylene polyoxyethylene block copolymer is 8,000; and the molecular weight of the polyoxypropylene polyoxyethylene random copolymer is 10,000.

The preparation method of the absorbable bone wax having a function of promoting bone repair in this example includes the following steps:
(1) Mixing the polyoxypropylene polyoxyethylene block copolymer and the polyoxypropylene polyoxyethylene random copolymer, and heating to 60° C. under a condition of mechanical stirring so that a resultant mixture is in a liquid state and is mixed well;
(2) Putting the well-mixed mixture in a mold or sub-packaged bottle, and leaving the mold or sub-packaged bottle at room temperature for 2 hours for curing and forming; and
(3) Packaging and sealing the cured and formed product and sterilizing it by autoclaving or γ-ray to obtain the absorbable bone wax.

EXAMPLE 7

As an example of the absorbable bone wax having a function of promoting bone repair according to the present invention, the absorbable bone wax having a function of promoting bone repair described in this example comprises the following components in mass percentage: 10% polyoxypropylene polyoxyethylene block copolymer, 50% polyoxypropylene polyoxyethylene random copolymer, 20% strontium substituted nano-hydroxyapatite, and 20% nano-microcrystalline cellulose, wherein the molar ratio of Sr/(Sr+Ca) in the strontium substituted nano-hydroxyapatite is 20%; the molecular weight of the polyoxypropylene polyoxyethylene block copolymer is 10,000; and the molecular weight of the polyoxypropylene polyoxyethylene random copolymer is 8,000.

The preparation method of the strontium substituted nano-hydroxyapatite described in this example includes the following steps:
1) Weighing a certain amount of $Ca(NO_3)_2 \cdot 4H_2O$ and dissolving it with deionized water in a beaker, weighing a certain amount of $Sr(NO_3)_2$ and dissolving it with deionized water in another beaker, adding $Sr(NO_3)_2$ solution into $Ca(NO_3)_2 \cdot 4H_2O$ suspension, adjusting the pH value of the resultant suspension of $Ca(NO_3)_2 \cdot 4H_2O$ and $Sr(NO_3)_2$ to be 11 or greater using $NH_3 \cdot H_2O$ solution, and then adding an appropriate amount of SDS to the resultant suspension, and mechanically stirring the solution containing $Ca^{2+}$ and $Sr^{2+}$;
2) Weighing a certain amount of $(NH_4)_2HPO_4$ and dissolving it in a beaker with deionized water to form a solution containing P;
3) Adding the $(NH_4)_2HPO_4$ solution dropwise into the solution containing $Ca^{2+}$ and $Sr^{2+}$ within 40 minutes, wherein the molar ratio of (Ca+Sr) to P in the final solution is 1.67; and transferring the resultant mixture into a high-pressure reactor for incubating for 8 hours at 180° C., then cooling it to about 25° C.;
4) Centrifuging the resultant solution at 10,000 rpm for 10 minutes, then performing pumping filtration, and washing sediment with deionized water and ethanol repeatedly; and
5) Drying the sediment in an oven at 80° C. for 12 hours and grinding it to obtain strontium substituted nano-hydroxyapatite (Sr-nHAp).

The preparation method of the absorbable bone wax having a function of promoting bone repair in this example includes the following steps:
(1) Mixing the polyoxypropylene polyoxyethylene block copolymer and the polyoxypropylene polyoxyethylene random copolymer, and heating to 90° C. under a condition of mechanical stirring so that a resultant mixture is in a liquid state and is mixed well;
(2) Under the condition of mechanical stirring and heating, adding nano-microcrystalline cellulose and strontium substituted nano-hydroxyapatite to the well-mixed liquid mixture in step (1), and then stirring and mixing well;
(3) Putting the well-mixed mixture in a mold or sub-packaged bottle, and leaving the mold or sub-packaged bottle at room temperature for 2 hours for curing and forming; and
(4) Packaging and sealing the cured and formed product and sterilizing it by autoclaving or γ-ray to obtain the absorbable bone wax.

EXAMPLE 8

As an example of the absorbable bone wax having a function of promoting bone repair according to the present invention, the absorbable bone wax having a function of promoting bone repair described in this example comprises the following components in mass percentage: 25% polyoxypropylene polyoxyethylene block copolymer, 60% polyoxypropylene polyoxyethylene random copolymer, 6% strontium substituted nano-hydroxyapatite, and 9% nanocrystalline cellulose, wherein the molar ratio of Sr/(Sr+Ca) in the strontium substituted nano-hydroxyapatite is 50%; the molecular weight of the polyoxypropylene polyoxyethylene block copolymer is 146,000; and the molecular weight of the polyoxypropylene polyoxyethylene random copolymer is 2,500.

The preparation method of the strontium substituted nano-hydroxyapatite described in this example includes the following steps:
1) Weighing a certain amount of $Ca(NO_3)_2 \cdot 4H_2O$ and dissolving it with deionized water in a beaker, weighing a certain amount of $Sr(NO_3)_2$ and dissolving it with deionized water in another beaker, adding $Sr(NO_3)_2$ solution into $Ca(NO_3)_2 \cdot 4H_2O$ suspension, adjusting the pH value of the resultant suspension of $Ca(NO_3)_2 \cdot 4H_2O$ and $Sr(NO_3)_2$ to be 11 or greater using $NH_3 \cdot H_2O$ solution, and then adding an appropriate amount of SDS to the resultant suspension, and mechanically stirring the solution containing $Ca^{2+}$ and $Sr^{2+}$;
2) Weighing a certain amount of $(NH_4)_2HPO_4$ and dissolving it in a beaker with deionized water to form a solution containing P;
3) Adding the $(NH_4)_2HPO_4$ solution dropwise into the solution containing $Ca^{2+}$ and $Sr^{2+}$ within 40 minutes, wherein the molar ratio of (Ca+Sr) to P in the final solution is 1.67; and transferring the resultant mixture into a high-pressure reactor for incubating for 8 hours at 180° C., then cooling it to about 25° C.;
4) Centrifuging the resultant solution at 10,000 rpm for 10 minutes, then performing pumping filtration, and washing sediment with deionized water and ethanol repeatedly; and
5) Drying the sediment in an oven at 80° C. for 12 hours and grinding it to obtain strontium substituted nano-hydroxyapatite (Sr-nHAp).

The preparation method of the absorbable bone wax having a function of promoting bone repair in this example includes the following steps:
(1) Mixing the polyoxypropylene polyoxyethylene block copolymer and the polyoxypropylene polyoxyethylene random copolymer, and heating to 100° C. under a condition of mechanical stirring so that a resultant mixture is in a liquid state and is mixed well;
(2) Under the condition of mechanical stirring and heating, adding nano-microcrystalline cellulose and strontium substituted nano-hydroxyapatite to the well-mixed liquid mixture in step (1), and then stirring and mixing well;
(3) Putting the well-mixed mixture in a mold or sub-packaged bottle, and leaving the mold or sub-packaged bottle at room temperature for 2 hours for curing and forming; and
(4) Packaging and sealing the cured and formed product and sterilizing it by autoclaving or γ-ray to obtain the absorbable bone wax.

COMPARATIVE EXAMPLE 1

The absorbable bone wax having a function of promoting bone repair described in this Comparative Example 1 is basically the same as that of Example 4, except that in this Comparative Example 1, the strontium substituted nano-hydroxyapatite is replaced by nano-hydroxyapatite.

The preparation method of the nano-hydroxyapatite described in this Comparative Example 1 includes the following steps:
1) Weighing a certain amount of $Ca(NO_3)_2 \cdot 4H_2O$ and dissolve it with deionized water, adjusting the pH value of the $Ca(NO_3)_2 \cdot 4H_2O$ solution to 11 or greater using $NH_3 \cdot H_2O$ solution, and adding SDS thereto to form a solution containing Ca;
2) Weighing a certain amount of $(NH_4)_2HPO_4$ and dissolve it with deionized water, adjusting the pH value of the $(NH_4)_2HPO_4$ solution to be 10 or greater using $NH_3 \cdot H_2O$ solution to form a solution containing P;
3) Under mechanical stirring, adding the $(NH_4)_2HPO_4$ solution dropwise into the $Ca(NO_3)_2 \cdot 4H_2O$ solution within 30 minutesm wherein the molar ratio of Ca to P in the final solution is 1.67, after stirring well, transferring the resultant mixture into a high-pressure reactor for incubating for 8 hours at 180° C., and then cooling it to about 25° C.;
4) Centrifuging the resultant solution at 10,000 rpm for 10 minutes, performing vacuum filtration, and washing sediment repeatedly with deionized water and ethanol; and
5) Drying the sediment in an oven at 80° C. for 12 hours and grinding it to obtain nano-hydroxyapatite (nHAp).

1. TEM Morphology Observation

The microscopic morphology of particles are observed by using TEM. FIG. 1A is a TEM image of nHAp particles in Comparative Example 1; and FIG. 1B is a TEM image of 10% Sr-nHAp in Example 1. It can be seen from the figures that the 10% Sr-nHAp in Example 1 has a bar-like structure with a length ranging from 80 nm to 220 nm and a width of approximately 22 nm; and the nHAp particle has a bar-like structure with a length range slightly longer than that of 10% Sr-nHAp and a width slightly wider than that of 10% Sr-nHAp.

2. Cell Activity

The cell viability of the absorbable bone wax of Example 1 to Example 8 is detected by the CCK-8 method. The cells used in this experiment are fibroblasts (3T3 cells), and the culture medium used for cultivating the cells is the MEM culture medium containing 10% fetal bovine serum and 1% double antibody (a mixed solution of penicillin and streptomycin). The cultivation is performed in an incubator at a temperature of 37° C. with a $CO_2$ concentration of 5%. In the process of cultivation, the cell culture medium should be changed every two days in order to provide new nutrients for the cells and remove non-adherent cells and cell metabolites. The sterilized absorbable bone wax of the respective examples are placed in a 48-well plate, then 50 μL of the treated cell suspension is added dropwise onto the absorbable bone wax. After cultivation in the incubator for 2 hours, 450 μL of the respective culture solution are added onto each group of scaffolds for further cultivation. CCK-8 reagent is respectively added in a ratio of 1:10 after 1, 4, 7 and 10 days of cultivation for further cultivation for 2 to 4 hours, i.e., 10 μL of CCK-8 reagent is added into 100 μL of culture solution. At 450 nm wavelength, the absorbance value of each well is read using a microplate reader. As shown in FIG. 2, the absorbable bone wax of the present invention has good biocompatibility, and the addition of strontium substituted nano-hydroxyapatite and the nano-microcrystalline cellulose significantly improves the biological activity of the absorbable bone wax.

3. APTT and PT Detection

The activated partial thromboplastin time (hereinafter referred to as APTT) and prothrombin time (hereinafter referred to as PT) of the mixture of absorbable bone wax extract and plasma are measured by a whole blood analyzer. The healthy anticoagulated blood is centrifuged at 1,000×g for 10 min, and the supernatant is collected. 180 μL of plasma is mixed with 20 μL of PBS or absorbable bone wax extract, the corresponding reagents are added thereto at 37° C., and then the resultant mixture is analyzed by a coagulation analyzer analysis with the analysis performed 3 times in parallel. The activated partial thromboplastin time (APTT) and prothrombin time (PT) of the absorbable bone wax of Example 1 to Examples 5 is determined, and the results are shown in FIG. 3. The results show that the prepared absorbable bone wax has good blood compatibility.

4. In Vivo Hemostasis Experiment 3-month-old male New Zealand rabbits are divided to five groups, i.e., Groups 1 to 5. The rabbits are shaved before operation on the tibial part of the right hind limb, and are anesthetized by intramuscularly injecting ketamine injection (25.0 mg/kg). After the rabbits are anesthetized, the operated sites are disinfected using povidone iodine. The skin and subcutaneous tissue of the tibia of the right hind limb are cut along the midline to expose the front of the tibia of the right posterior limb. A bone defect area of 4.2 mm in diameter and 3 mm in depth is drilled at 4 cm below the knee joint. After the model is successfully established, take a photo, and then the test substance is immediately applied to the bone defect area. The duration from the time when the test substance is applied to the defect area to the time when bleeding stops is recorded. The in vivo hemostatic effect of the absorbable bone wax of Example 1 to Example 5 are shown in FIGS. 4A-4E, and it can be seen that the absorbable bone wax of the present invention has good hemostatic properties.

5. Coagulation Parameters

TABLE 1

| Sample | R (min) | K (min) | α (deg) | MA (mm) |
| --- | --- | --- | --- | --- |
| Normal range | 5~10 | 1~3 | 53~72 | 50~70 |
| Example 1 | 6.5 | 2.3 | 52.4 | 55.9 |
| Example 2 | 5.3 | 2.8 | 60.3 | 57.8 |
| Example 3 | 5.8 | 1.6 | 63.5 | 61.7 |
| Example 4 | 5.5 | 2.1 | 61.7 | 66.2 |
| Example 5 | 5.3 | 2.1 | 66 | 58.9 |
| Example 6 | 5.5 | 2.0 | 62.2 | 59.3 |

TABLE 1-continued

| Sample | R (min) | K (min) | α (deg) | MA (mm) |
|---|---|---|---|---|
| Example 7 | 5.7 | 1.8 | 61.6 | 61.4 |
| Example 8 | 5.4 | 1.8 | 62.5 | 63.7 |

The coagulation parameters of the absorbable bone wax of Example 1 to Example 8 are shown in Table 1. The R values of the absorbable bone wax of the present invention are in a range from 5.3 to 6.5 min, which is lower than the normal range of 5 to 10 min. The absorbable bone wax of the present invention has a procoagulant effect on blood.

6. Hemostasis Time

TABLE 2

| Sample | Example 1 | Example 2 | Example 3 | Example 4 | Example 5 | Example 6 | Example 7 | Example 8 |
|---|---|---|---|---|---|---|---|---|
| Hemostasis time (s) | 8.2 | 7.1 | 7.8 | 5.5 | 3.0 | 5.2 | 4.5 | 6.1 |

The hemostasis times of the absorbable bone wax of Example 1 to Example 8 are shown in Table 2. The hemostasis time of the absorbable bone wax of the present invention are in a range from 3.0 to 8.2 seconds, indicating a good hemostatic effect.

7. Mechanical Performance Testing

According to test methods of the Pharmaceutical Industry Standard YY/T 0471.4-2004 in China, a universal testing machine is used to determine compressive strength and compressive stress of the absorbable bone wax numbered 1 to 5. The load-bearing capacity is 500 N, and the efficiency is within ±1%. The specific steps are as follows: cutting the absorbable bone wax into samples with a length of 50 mm, a width of 50 mm, and a height of 20 mm; measuring and recording thicknesses of the samples with a vernier caliper; performing compression under constant temperature and constant humidity condition (the temperature is 25° C., and the relative humidity is 70%), with a clamping distance of the samples of 20 mm and the compression rate of 300 mm/min; setting procedures according to the test methods to perform tests, and obtaining 5 groups of valid data for each test, and calculating average values thereof. The compressive strength of the absorbable bone wax of Example 1 to Example 8 and Comparative Example 1 are shown in Table 3. Compared with chitosan used in prior art, interaction between nano-crystalline cellulose and strontium substituted nano-hydroxyapatite enhances mechanical strength of the absorbable bone wax, and the nano-crystalline cellulose contributes to regeneration and healing of bone tissues by the strontium substituted nano-hydroxyapatite.

TABLE 3

| No. | Compressive stress (MPa) | Compression modulus (MPa) |
|---|---|---|
| Example 1 | 0.24200 ± 0.03156 | 0.99442 ± 0.23169 |
| Example 2 | 0.24525 ± 0.01629 | 2.65257 ± 1.04097 |
| Example 3 | 0.23401 ± 0.02384 | 2.94196 ± 1.66073 |
| Example 4 | 0.31108 ± 0.05709 | 3.61731 ± 1.27957 |
| Example 5 | 0.26031 ± 0.05163 | 6.11471 ± 2.90457 |
| Example 6 | 0.23121 ± 0.05683 | 2.35431 ± 1.22487 |
| Example 7 | 0.29863 ± 0.05854 | 2.66231 ± 1.35842 |
| Example 8 | 0.25086 ± 0.05624 | 1.91781 ± 1.29864 |
| Comparative Example 1 | 0.24452 ± 0.04642 | 3.03245 ± 1.34545 |

8. Alkaline Phosphatase (ALP) Activity Detection

Figure 5:
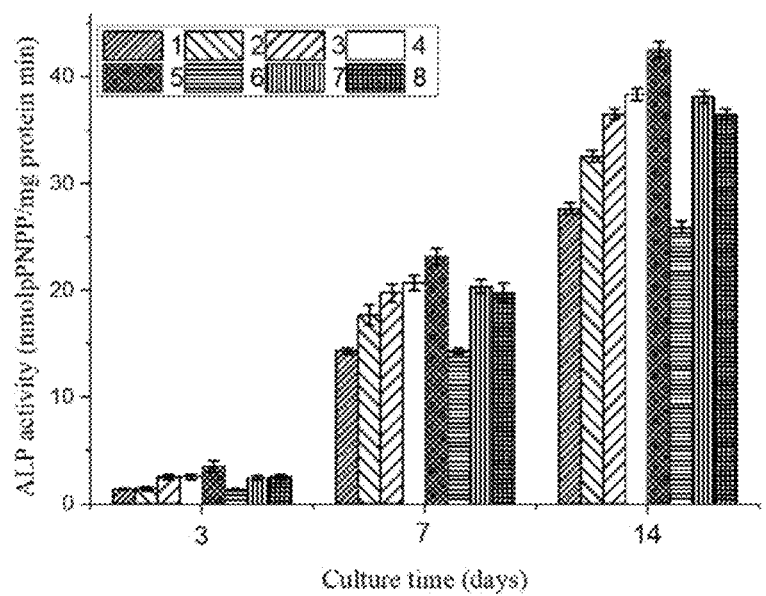
FIG. 5 is an ALP activity diagram of bone wax of Example 1 to Example 5.

The sterilized absorbable bone wax of the different groups is placed into a 48-well culture plate. The cells cultured to the third generation are digested and separated from a culture flask with 0.25% pancreatin and centrifuged at 1,000 rpm for 5 minutes, the supernatant is discarded, then α-DMEM medium containing serum and double antibody (a mixed solution of penicillin and streptomycin) is added into the cells, and the cell concentration is adjusted to $5\times10^7$ cells per milliliter. Each of the absorbable bone wax samples inoculated with 20 μL of the above cell suspension is cultivated in an incubator having 5% $CO_2$ at 37° C. for 2 hours, and then 500 μL of the culture medium is added thereto for further cultivation for 7 days and 14 days. During the cultivation period, the culture medium is changed every 2 to 3 days to provide sufficient nutrients for the cells. The scaffold is removed from the well plate, the absorbable bone wax is rinsed 3 times with sterile PBS solution, 500 μL of cell lysate is added therein, and then the resultant mixture is placed in an ultrasonic cell disruptor at a temperature of 4° C. for cell disruption. The disrupted cells are centrifuged, and the supernatant is collected and added with 500 μL of the ALP substrate reaction solution to react for 30 min in water bath at a temperature of 37° C. 500 μL of 0.1M NaOH is added into the reaction solution to stop the reaction, and then the spectrophotometric values of the samples at 405 nm are measured by a UV-visible spectrophotometer, and the ALP is calculated according to the instruction of the manual. The absorbable bone wax of each group at each time point is tested at least 3 times in parallel. The experimental results are shown in FIG. 5. The ALP activities of the cells in the absorbable bone wax of Example 1 to Example 8 show an increasing trend with the extension of the incubation time. The experimental results show that the absorbable bone wax of Example 1 to Example 8 is conducive to osteogenesis differentiation.

In summary, the absorbable bone wax of the present invention has good biocompatibility and a blood coagulation effect, can accelerate wound healing, and effectively promotes growth of bone tissues.

Finally, it should be noted that the above embodiments are only used to illustrate the technical solutions of the present invention and not to limit the protection scope of the present invention. Although the present invention has been described in detail with reference to preferred embodiments, those skilled in the art should understand that, modifications or equivalent replacements could be made to the technical solutions of the present invention without departing from the spirit and scope of the technical solution of the present invention.

What is claimed is:

1. Absorbable bone wax having a function of promoting bone repair, wherein the absorbable bone wax comprises the following components in mass percentage: 10%-30% polyoxypropylene polyoxyethylene block copolymer, 50%-65% polyoxypropylene polyoxyethylene random copolymer, 2.5%-20% strontium substituted hydroxyapatite and 2%-20% microcrystalline cellulose, a molar ratio of Sr/(Sr+

Ca) in the strontium substituted hydroxyapatite is in a range from 10% to 50%, the strontium substituted hydroxyapatite is strontium substituted nano-hydroxyapatite prepared by a co-precipitation method, and the microcrystalline cellulose is nano-crystalline cellulose.

2. The absorbable bone wax having a function of promoting bone repair according to claim 1, wherein the absorbable bone wax comprises the following components in mass percentage: 30% polyoxypropylene polyoxyethylene block copolymer, 65% polyoxypropylene polyoxyethylene random copolymer, 2.5% strontium substituted hydroxyapatite and 2.5% microcrystalline cellulose.

3. The absorbable bone wax having a function of promoting bone repair according to claim 1, wherein a molecular weight of the polyoxypropylene polyoxyethylene block copolymer is in a range from 4,400 to 14,600; and a molecular weight of the polyoxypropylene polyoxyethylene random copolymer is in a range from 2,500 to 12,000.

4. The absorbable bone wax having a function of promoting bone repair according to claim 2, wherein a molecular weight of the polyoxypropylene polyoxyethylene block copolymer is in a range from 4,400 to 14,600; and a molecular weight of the polyoxypropylene polyoxyethylene random copolymer is in a range from 2,500 to 12,000.

5. A preparation method of absorbable bone wax having a function of promoting bone repair according to claim 1, wherein the preparation method comprises the following steps:
   (1) Mixing polyoxypropylene polyoxyethylene block copolymer and polyoxypropylene polyoxyethylene random copolymer, and heating to a temperature in a range from 60° C. to 100° C. under a condition of mechanical stirring so that a resultant mixture is in a liquid state and is mixed well;
   (2) While maintaining conditions of mechanical stirring and heating, adding nano-microcrystalline cellulose and strontium substituted nano-hydroxyapatite into a well-mixed liquid mixture in step (1), and stirring and mixing well;
   (3) Putting a well-mixed mixture in step (2) in a mold or sub-packaged bottle, and leaving the mold or sub-packaged bottle at room temperature for 2 hours for curing and forming; and
   (4) Packaging and sealing a cured and formed product, and sterilizing it by autoclaving or γ-ray to obtain the absorbable bone wax.

\* \* \* \* \*